US00PP37347P2

(12) United States Plant Patent
Ioriatti

(10) Patent No.: US PP37,347 P2
(45) Date of Patent: Mar. 31, 2026

(54) ***FRAGARIA* PLANT NAMED 'BTSB One'**

(50) Latin Name: *Fragaria ananassa*
Varietal Denomination: BTSB one

(71) Applicant: Berrytech SRL, Baselga di Pine (IT)

(72) Inventor: Diego Ioriatti, Baselga di Pine (IT)

(73) Assignee: Berrytech SRL (IT)

( * ) Notice: Subject to any disclaimer, the term of this patent is extended or adjusted under 35 U.S.C. 154(b) by 0 days.

(21) Appl. No.: 19/267,833

(22) Filed: Jul. 14, 2025

(51) Int. Cl.
*A01H 5/08* (2018.01)

(52) U.S. Cl.
USPC ..... Plt./209

(58) Field of Classification Search
USPC ..... Plt./209
CPC ..... A01H 6/7409; A01H 5/08
See application file for complete search history.

*Primary Examiner* — Keith O. Robinson

(57) ABSTRACT

A new and distinct cultivar of *Fragaria* plant named 'BTSB One' is disclosed, characterized by conical, uniformly sized fruits. Plants are semi-erect, including the lateral branches. Fruit has a clear light red color which is maintained during post-harvest. The new cultivar is a *Fragaria*, intended for commercial fruit production.

3 Drawing Sheets

Figure 1:
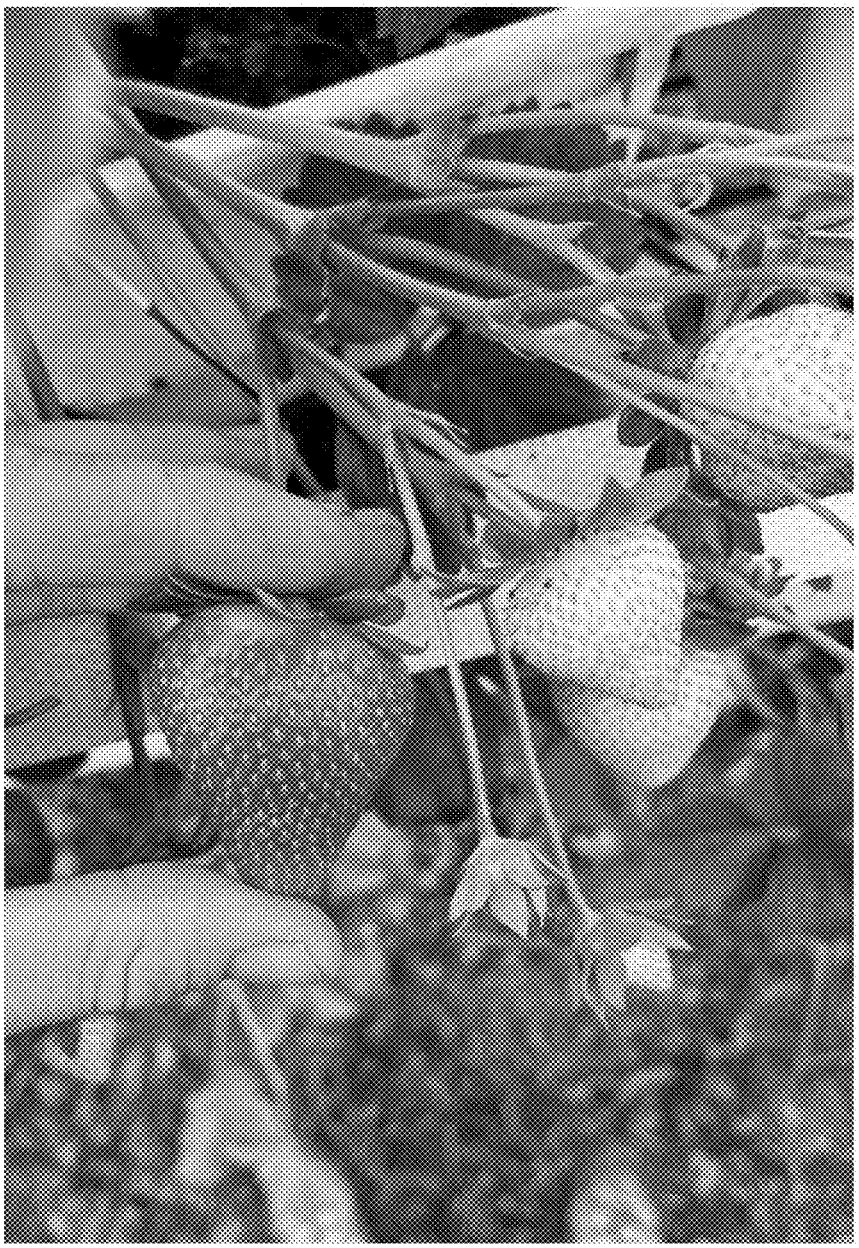

Latin name of the genus and species: *Fragaria ananassa.*
Variety denomination: 'BTSB ONE'.

BACKGROUND OF THE INVENTION

The new *Fragaria* cultivar is a product of a planned breeding program conducted by the inventor, in Trentino Alto Adige, Italy. The objective of the breeding program was to produce new *Fragaria* varieties for commercial fruit production.

The seed parent is an unpatented, proprietary variety referred to as 'BT15-01'. The pollen parent an unpatented, proprietary variety referred to as 'BT17ST120'. The cross resulting in 'BTST ONE' was made around July 2020. The initial selection was made during 2021.

Asexual reproduction of the new cultivar was first performed by vegetative runners. This was first performed at a research greenhouse in Verona, Italy in Summer of 2021. Subsequent propagation has shown that the unique features of this cultivar are stable and reproduced true to type in multiple successive generations.

SUMMARY OF THE INVENTION

The cultivar 'BTSB ONE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BTSB ONE'. These characteristics in combination distinguish 'BTSB ONE' as a new and distinct *Fragaria* cultivar:

1. Uniform fruit size throughout the fruiting season.
2. Improved remontancy of flowering compared to most current cultivars at the date of selection, with a reduced gap of fruiting period after the first harvest based on June-bearing flower induction.
3. Light color of the fruits even at an advanced ripening stage.

4. Fruit glossiness during the fruiting season.

PARENT COMPARISON

Plants of the new cultivar 'BTSB ONE' are similar to plants of the seed parent, in most horticultural characteristics, however, plants of the new cultivar 'BTSB ONE' differ in the following:

1. The new cultivar produces fruit which is more consistent in both size and color than the seed parent.
2. The new cultivar produces fruit that is not affected by "green tip" or misshapen fruit as can happen in the seed parent.
3. The new cultivar produces firmer fruits in warm temperatures than the seed parent.
4. The new cultivar produces smaller fruits on average than the seed parent.
5. The new cultivar produces flowers on shorter pedicels than the seed parent.
6. Plants of the new cultivar are shorter than plants of the seed parent.
7. The new cultivar produces less fruits per season, but, production is spread more evenly over the fruiting season.

Plants of the new cultivar 'BTSB ONE' are similar to plants of the pollen parent, in most horticultural characteristics, however, plants of the new cultivar 'BTSB ONE' differ in the following:

1. The new cultivar produces fruit which is more consistent in both size and color than the pollen parent.
2. The new cultivar produces fruit that is not affected by "green tip" or misshapen fruit as can happen in the pollen parent.
3. The new cultivar produces larger fruits than the pollen parent.
4. Fruits of the new cultivar are lighter in color than fruits of the pollen parent.

COMMERCIAL COMPARISON

Plants of the new cultivar 'BTSB ONE' are comparable to the patented commercial variety *Fragaria* 'Portola' U.S.

Plant Pat. No. 20,552. The two *Fragaria* varieties are similar in most horticultural characteristics; however, the new variety 'BTSB ONE' differs in the following:

1. The new variety produces less fruit than 'Portola' with an estimated overall productivity of 10 to 15% less fruit produced than 'Portola'. It appears 'BTSB ONE' is less productive with first remontant fruits after June-bearer production; 'Portola' has more consistent continuous production.
2. The new variety produces fruit with a higher brix level than 'Portola'. 'BTSB ONE' has a brix level of about 8 compared to brix level of 6.5 to 7 measured in fruit of 'Portola'.
3. The new variety produces fruit which is lighter red than 'Portola' under any growing conditions.
4. In warm conditions the new variety shows more fragile fruit skin than 'Portola'.

Plants of the new cultivar 'BTSB ONE' are comparable to the patented commercial variety *Fragaria* 'Favori' unpatented. The two *Fragaria* varieties are similar in most horticultural characteristics; however, the new variety 'BTSB ONE' differs in the following:

1. The new variety shows higher productivity in the period of first remontant fruits after June-bearer production than 'Favori'.
2. The new variety has larger foliage than 'Favori'.
3. The new variety produces larger fruits than 'Favori'.
4. Fruits of the new variety are a broader conical than fruits of 'Favori'.

BRIEF DESCRIPTION OF THE PHOTOGRAPHS

This new *Fragaria* is illustrated by the accompanying photographs which show the plant's form, foliage and inflorescences. The photographs were taken using conventional techniques and although colors may appear different from actual colors cited due to faults caused by conventional photographic techniques.

FIG. 1: illustrates in full color a typical ripe and unripe fruit of 'BTSB ONE' on the plant. Age of the plant photographed is approximately 6 to 8 months.

Figure 2:
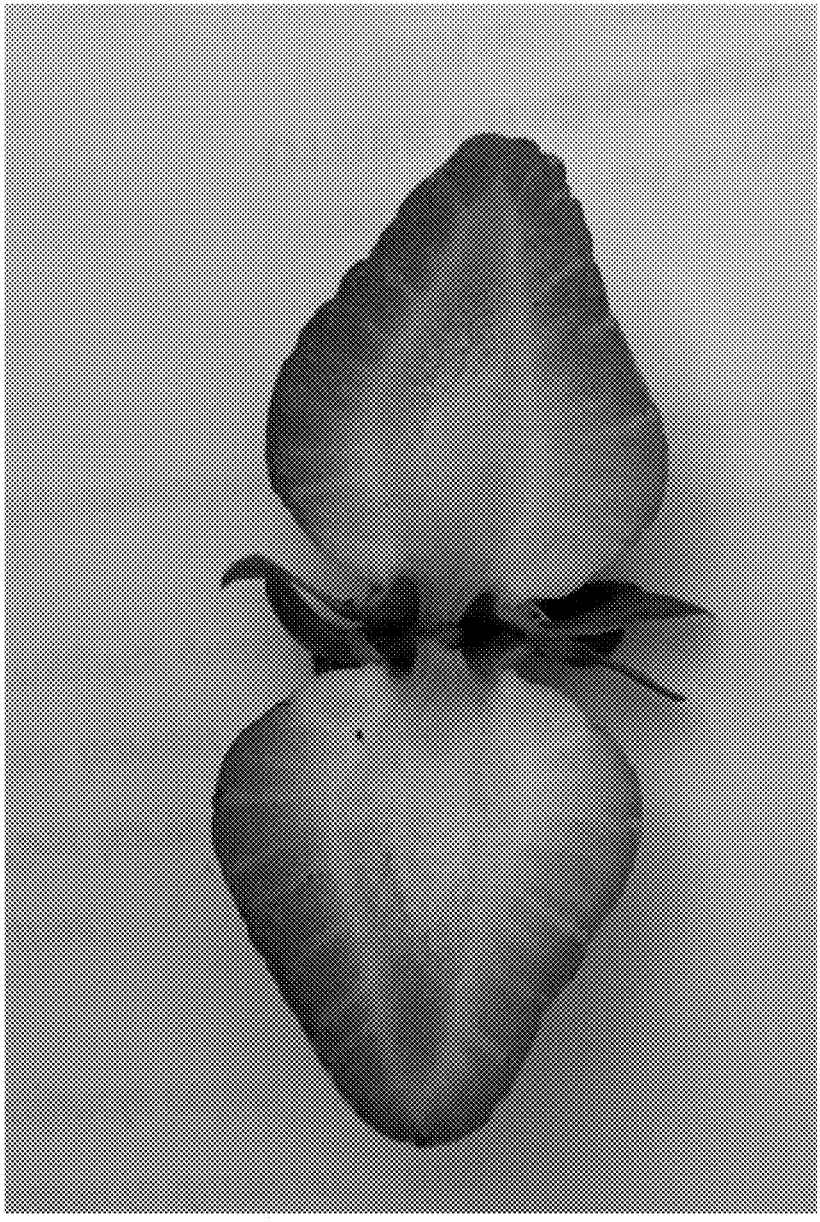

FIG. 2: illustrates a cross-section of the fruit.

Figure 3:
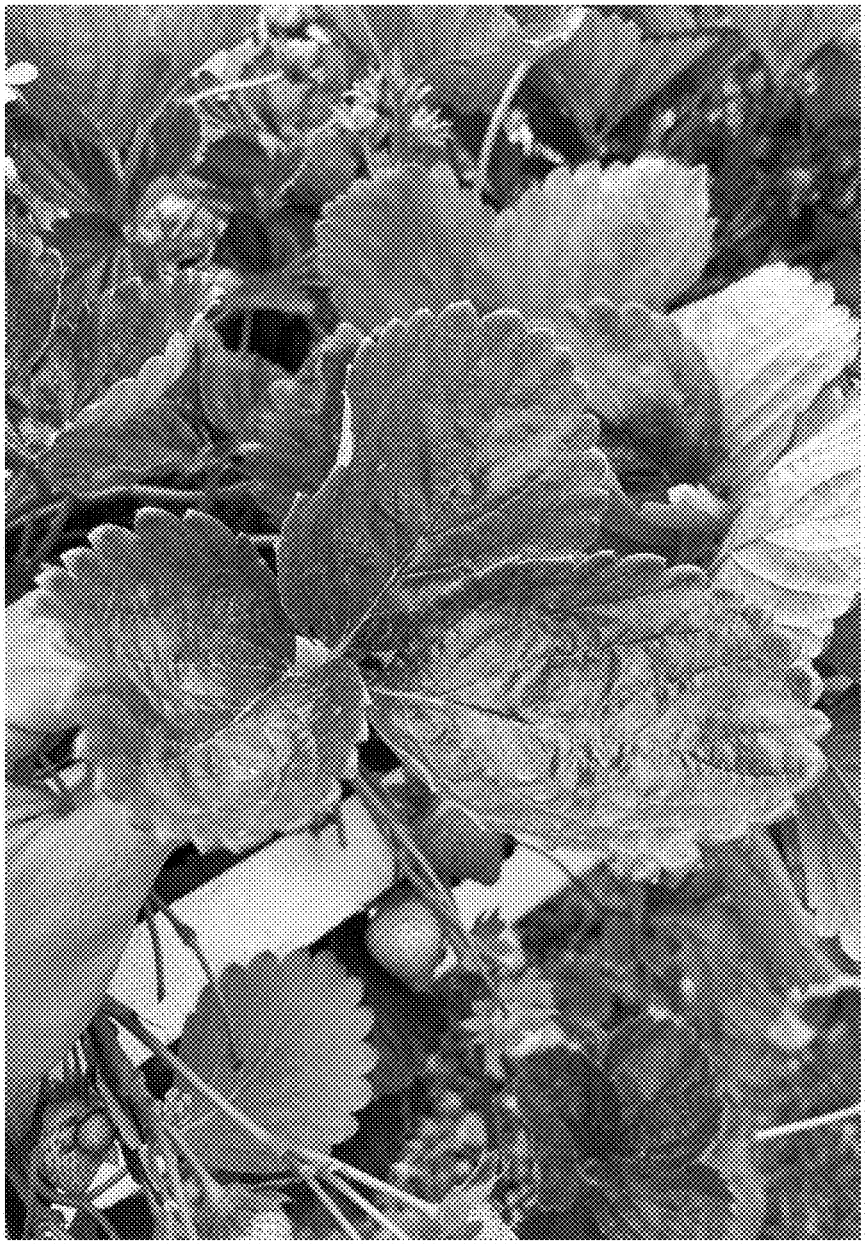

FIG. 3: illustrates a close-up view of the foliage.

DETAILED BOTANICAL DESCRIPTION

In the following description, color references are made to The Royal Horticultural Society Colour Chart 2019 except where general terms of ordinary dictionary significance are used. The following observations and measurements describe 'BTSB ONE' plants grown in the Summer of 2014, in open sided poly tunnels in Baselgia di Pine, Italy. No chemical treatments, including growth regulators were given. The growing temperature ranged from 20° C. to 36° C. during the day and from 12° C. to 30° C. during the night. General light conditions are bright, normal sunlight. Measurements and numerical values represent averages of typical plant types.

Botanical classification: *Fragaria* 'BTSB ONE'.

Propagation:

Type of propagation typically used: Runners are selected, cut and planted in moist conditions more times during the season. Mother plants are normally separated from flowers they carry in order to promote runner production. Runners are thus planted and kept below a regime of humidity, treatments and temperature controlled over the period of about 2 weeks for root induction and following period of plant acclimatation and hardening.

Root description: Roots appear moderately thick and rapidity of root growth is elevated.

Plant:

*Age of plant described.*—Approximately 2 years.
*Average crowns per plant.*—2 at first year of growth.
*Plant spread.*—30 to 35 cm.
*Plant height.*—20 to 23 cm.
*Habit.*—Semi-erect.
*Bract frequency.*—10 to 12 most commonly.
*Quantity of stolons.*—25 to 45 per plant.

Stolon:

*Diameter.*—Approximately 1 cm.
*Texture.*—Smooth, non-pubescent.
*Color.*—Near RHS Green 143A.

Foliage:

Leaf:

*Arrangement.*—Opposite.
*Leaf.*—Type: Typically a compound leaf with 3 leaflets. Average Length: 16.8 cm. Average Width: 21.5 cm. Attachment: Stalked.
*Leaflets.*—Quantity: 3. Average Length: 5.91 cm. Range between 5.25-6.28 cm. Average Width: 4.74 cm. Range between 4.06-5.29 cm. Shape of blade: Ovate. Aspect: Concave. Apex: Rounded and crenate. Base: Rounded. Attachment: Stalked. Margin: Serrate to Crenate. Appearance and texture of top surface: Slightly glossy, glabrous. Appearance and texture of underside: Glabrous, matte. Rugosity: Weak.
*Color.*—Mature foliage upper side: Near RHS Green N137 D. Mature foliage under side: Near RHS Green N138 C.

Petiole:

*Length.*—2 cm.
*Diameter.*—0.57 cm.
*Pubescence.*—Medium density.
*Color.*—Near RHS Yellow-Green 145 C.

Petiolule:

*Length.*—1 to 3.5 cm.
*Diameter.*—4 mm.
*Pubescence.*—Scant.
*Color.*—Near RHS Yellow-Green 149A.

Bracts present/frequency: 10 to 13 normally.

Stipule:

*Length.*—2 to 2.5 cm.
*Diameter.*—1.5 cm.

Flower:

Individual flowers:

*Type.*—Grouped in racemes, touching to overlapping petals.
*Position held on plant.*—Slightly lower than upper leaves.
*Calyx size in relation to the corolla.*—Slightly larger.
*Diameter.*—2.5 cm.
*Depth.*—0.8 cm.
*Bloom time.*—First week of May to November.

Bud:

*Shape.*—Globular.
*Length.*—Approximately 1.36 cm.
*Diameter.*—Approximately 1.4 cm.
*Color.*—Near RHS Yellow-Green 143C.

Petals:

*Quantity.*—6 to 7.

*Length.*—0.8 cm to 1.0 cm.

*Width.*—0.9 cm to 1.2 cm.

*Shape.*—Orbicular.

*Spacing.*—Touching, rarely overlapping.

*Color.*—When Opening: Upper Surface: Near RHS White 155A. Lower Surface: Near RHS White 155A. Fully Opened: Upper Surface: Near RHS White 155A. Lower Surface: Near RHS White 155A.

*Texture.*—Smooth and soft.

*Margin.*—Entire.

*Apex.*—Rounded, blunt.

*Base.*—Rounded.

Pedicel:

*Length.*—3 to 6 cm.

*Diameter.*—0.3 cm.

*Color.*—Near RHS Yellow-Green 145A.

Reproductive organs:

*Stigma color.*—Near RHS Yellow 2B.

*Style color.*—Near RHS Yellow 6B.

*Anther color.*—Near RHS Yellow 9A.

*Filament color.*—Near RHS White 155A.

Fruit:

*Predominant general shape.*—Conical.

*Type of bearing.*—Fully remontant.

*Variance in fruit shape between primary and secondary fruits.*—70-80%.

*Length.*—Average 4.3 cm.

*Width.*—Average 4.1 cm.

*Average typical quantity of berries per plant.*—35-40 overall fruiting over the season.

*Texture or evenness of fruit surface.*—Smooth and slightly fragile on skin during warm periods.

*Interior flesh color when ripe.*—Near RHS Orange-Red 33B.

*Evenness of flesh color.*—Consistently colored N30A.

*Exterior surface color when ripe, exterior.*—Top: Near RHS Orange-Red N30A. Side: Near RHS Orange-Red 33B.

*Achene color.*—Near RHS Yellow 13A.

*Achene quantity.*—300 to 350.

*Achene position.*—Below surface.

*Calyx insertion.*—Shallow.

*Fruit position of calyx attachment.*—Level with fruit.

*Size of calyx in relation to diameter of fruit.*—Slightly smaller to smaller.

*Color of calyx.*—Near RHS Yellow-Green 144C.

*Ease of calyx removal.*—Intermediate.

*Attitude of fruit sepals.*—Outwards.

*Firmness of flesh.*—Medium to slightly soft.

*Brix at consumption.*—8°.

*Brix at harvest.*—9°.

*Average weight.*—19 grams.

*Minimum weight.*—17 grams.

*Maximum weight.*—21 grams.

*Fruit peduncle length.*—35 mm.

*Fruit peduncle diameter.*—30 mm.

*Fruit peduncle color.*—Near RHS Yellow-Green 145B.

*Harvest time.*—First harvest: June 17. Last harvest: November 15. Overall cropping quantity: 1.2 kg per plant.

OTHER CHARACTERISTICS

Storage life: Storage life is a minimum of 5 days at 2° C.

Disease/pest resistance: Good tolerance to *Phytophtora* root rot. Neither resistance nor susceptibility to other normal diseases and pests of *Fragaria* have been observed to date.

Temperature tolerance: Extreme temperature tolerance not yet observed. Plants have been successfully grown under confidential test conditions in Italy.

What is claimed is:

1. A new and distinct cultivar of *Fragaria* plant named 'BTSB One' as herein illustrated and described.

* * * * *